United States Patent [19]

Baba et al.

[11] Patent Number: 4,654,139
[45] Date of Patent: Mar. 31, 1987

[54] FLOCCULATION BASIN IN WATER TREATMENT PROCESS

[75] Inventors: Kenji Baba; Shoji Watanabe; Shunsuke Nogita, all of Hitachi; Mikio Yoda, Tohkai; Akihiro Tanaka; Shunji Mori, both of Hitachi, all of Japan

[73] Assignee: Hitachi, Ltd., Tokyo, Japan

[21] Appl. No.: 742,560

[22] Filed: Jun. 7, 1985

[30] Foreign Application Priority Data

Jun. 8, 1984 [JP] Japan .............................. 59-116450
Jul. 3, 1984 [JP] Japan .............................. 59-136576
Jul. 3, 1984 [JP] Japan .............................. 59-136577
Jul. 4, 1984 [JP] Japan .............................. 59-137289

[51] Int. Cl.$^4$ .............................................. C02F 1/52
[52] U.S. Cl. ..................................... 210/85; 210/96.1; 210/143; 210/205; 210/255; 358/101; 364/502
[58] Field of Search ............... 210/702, 709, 738, 739, 210/745, 94, 96.1, 143, 205, 208, 219, 85, 255; 358/99, 101; 364/500, 555, 502

[56] References Cited

U.S. PATENT DOCUMENTS 3,731,807 5/1973 Louboutin et al. ............... 210/96.1
4,388,195 6/1983 von Hagel et al. ................ 210/709

FOREIGN PATENT DOCUMENTS

0019055 11/1980 European Pat. Off. .......... 210/96.1
55-67306 5/1980 Japan ................................. 210/96.1
57-38228 3/1982 Japan ................................. 364/555

Primary Examiner—Peter Hruskoci
Attorney, Agent, or Firm—Antonelli, Terry & Wands

[57] ABSTRACT

The fluidizing speed of water inside a flocculation basin of a water treatment process plant is adjusted in accordance with the state of flocculation inside the flocculation basin. The state of flocculation is determined by taking a plurality of pictures within a predetermined period by an ITV disposed inside the basin, recognizing a sufficiently large number of flocs from the pictures thus taken, calculating the particle diameters of the flocs and determining the particle diameter distribution from the result of calculation. The judgement signal is used as a signal for adjusting the water fluidizing speed.

14 Claims, 30 Drawing Figures

FLOCCULATION BASIN IN WATER TREATMENT PROCESS

BACKGROUND OF THE INVENTION

1. Field of the Invention

This invention relates to a flocculation basin in a water treatment process of clean water or sewage. More particularly, in a water treatment process for flocculating turbid small particles in water introduced into the basin to floating matters called "flocs", the present invention relates to a flocculation basin which accurately monitors the growth of the flocs and grows them stably and satisfactorily.

2. Description of the Prior Art

In a water treatment process, turbid fine particles are removed after coarse contents are removed. The fine particles make water turbid. Among the turbid fine particles, those which have large particle diameters can be removed by precipitation, but those having particle diameters of several microns can not be removed by precipitation. Therefore, a flocculant or coagulant is added to water in order to flocculate the fine particles to the mass of particles called "flocs", and the resulting flocs are thereafter removed by precipitation.

In the water treatment process of the kind described above, whether or not the flocs are formed satisfactorily affects directly the precipitation and filtration processes as subsequent treatment processes. If the flocculation is not good, the precipitativity of flocs in a settling basin drops. The drop of precipitativity in turn invites the overload of a filtering basin. If the detection of the overload is too late, a critical problem will develop in that the fine flocs flow out from the filtering basin.

SUMMARY OF THE INVENTION

It is an object of the present invention to provide a control apparatus for a flocculation basin which improves flocculation.

It is another object of the present invention to provide a floc monitor for a flocculation basin control apparatus which accurately monitors the growth of flocs in the flocculation basin, and further improves flocculation.

It is still another object of the present invention to provide a floc monitoring which further improves the monitor of flocculation.

One of the characterizing features of the present invention resides in that the state of flocculation in a flocculation basin is accurately monitored, and a flocculater for stirring the water inside the flocculation basin is controlled in accordance with the monitored state to change its fluidizing speed.

Another characterizing feature of the present invention resides in that image camera means for taking images of a predetermined area inside the flocculation basin is disposed, a plurality of images are picked up from the image camera means and the particle diameter distribution of flocs is determined from these images.

Still another characterizing feature of the present invention resides in that means for reducing the fluidizing speed of water flowing in the predetermined area is disposed in the proximity of the image camera means.

Still another characterizing feature of the present invention resides in that shading means is disposed in order to shield at least the area, which is covered by the image camera means, and to stably keep the intensity of illumination of such an area at a predetermined level.

DESCRIPTION OF THE PREFERRED EMBODIMENTS

Figure 1:
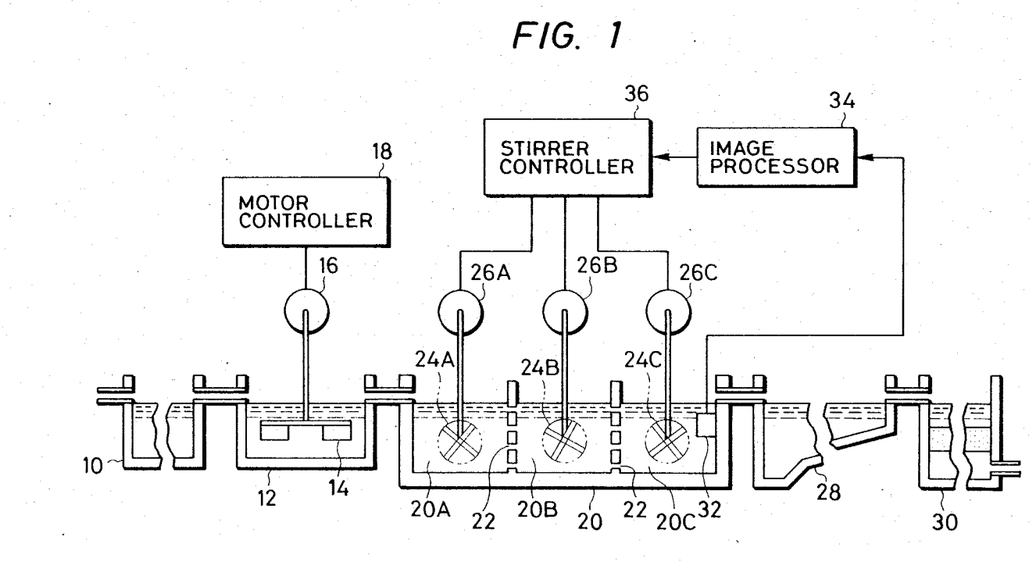
FIG. 1 is a schematic view showing the outline of a water treatment process including a flocculation basin and its control apparatus in accordance with one embodiment of the present invention.

FIG. 1 shows a water treatment process including a flocculation basin in accordance with one embodiment of the present invention. To have the present invention more clearly understood, a water purification process as an example of general water treatment processes will be explained with reference to FIG. 1 before describing in detail the present invention.

Raw water collected from an intake source such as a river flows through an intake and reaches a screen through a penstock, where wood chips, gravel, and the like, are removed. The raw water then reaches a grid chamber, where sand having large particle diameters are removed. (The process up to this stage is not shown in the drawing.)

The raw water is thereafter introduced into a water basin 10 in a purification plant, and chlorine is added to the water so that the raw water is sterilized and iron, manganese, and the like, are oxidized. The raw water is then introduced into a flush mixer 12, where coagulants such as alum, PAC (polyaluminum chloride), and the like, are added. A mixer 14 is driven by a motor 16 in the flush mixer 12 to promote mixing between the water and the coagulants. A motor controller for the motor 16 is represented by reference numeral 18. After the coagulants are added, the water is sent to a flocculation basin 20. Fine particles in the raw water flocculate inside the flocculation basin 20 and form flocs.

Although the flocculation basin 20 consists of a plurality of basins, the basin 20 in this embodiment consists of three flocculation basins 20A, 20B and 20C. A plurality of, or single, flocculation basin will be hereinafter called merely the "flocculation basin". The flocculation basin 20A, 20B, 20C is cascaded by a flow passage 22. A flocculater having a floc agitation paddle 24A, 24B, 24C is disposed in the flocculation basin 20A, 20B, 20C to stirr the flocs. Each paddle 24A, 24B, 24C has blades of a criss-cross arrangement and is driven by a motor 26A, 26B, 26C to stir the flocs. The flow passage 22 has also the function of a rectification wall. Although the flow passage 22 in this embodiment consists of a large number of communication holes disposed to extend from the upper portion to the bottom of the flocculation basin 20, only part may be used, too.

The raw water and the groups of fine flocs contained in the former flow into the flocculation basin 20. The paddle 24A, 24B, 24C stirs the water in the flocculation basin 20A, 20B, 20C in the longitudinal direction of the basin (that is, from the surface to the reverse of the sheet of the drawing), and causes the flocs to impinge against one another. The flocs gradually flocculate by the impingement with the aid of the coagulant, and their particle diameters become gradually greater. The flocs in the flocculation basin 24B is greater than those in the flocculation basin 24A, and the flocs in the flocculation basin 24C are greater than those in the flocculation basin 24B. In other words, the particle diameters of the flocs increase with an increasing number of flocculation basins.

The water containing the grown flocs is sent to a settling basin 28, where the flocs are settled and removed. The fine particles that are not removed in the settling basin 28 are removed substantially completely in a next filtration basin 30. In this basin 30, bacterias and microorganisms are also removed together with the fine particles. After the fine particles and the like are thus removed, the filtered water is sent to a chlorinater (not shown), where sterilization and the adjustment of alkalinity are effected by adding chlorine and an alkaline agent. Thereafter, the water is sent to a distributing reservoir (not shown) and is supplied to each user as a product.

In the water treatment process having the construction described above, the flocculation state of the flocculation basin significantly affects each of the subsequent precipitation and filtration processes, as described already.

As described previously, the flocs are fluidized by the revolution of the paddle 24A, 24B, 24C, impinge against one another and grow to greater flocs. However, it is known that if the revolution of the paddle 24A, 24B, 24C is too strong, the flocs will be destroyed by the shear force of a turbulent flow and do not grow to greater flocs.

The floc particle diameter and the number of revolution of the paddle have the following relation as described, for example, in the reference (Service Water Association Report, No. 441, June, 1971):

$$d_{max} \propto U - \frac{9}{2(3 + K\rho)} \quad (1)$$

where $d_{max}$ : maximum floc particle diameter that can be grown,

U: number of revolution of paddle, $K\rho$: coefficient.

This equation represents that the smaller the number of revolution of the paddle, the smaller become flocs.

If the revolution of the paddle 24A, 24B, 24C is too weak, on the contrary, the frequency of mutual impingement of the flocs drops so that all the floc particles can not grow to greater flocs within a predetermined period (in the retention time in the flocculation basin). In other words, if agitation is too weak, the turbid particles will remain as such and the major proportion of flocs turn out to be fine flocs, even though greater flocs can be formed partially.

Therefore, in this embodiment of the present invention, a floc monitor for monitoring the growth state of flocs is disposed in the third flocculation basin 20C. The floc monitor consists of an imaging device 32 such as an industrial television (ITV) which picks up the flocculation state in the water as images, and an image processor 34 which processes the image information signals from the imaging device 32 and judges the growth state of flocs.

The image processor 34 measures the particle diameters of the flocs, calculates the particle diameter distribution and its characteristic values, and produces them as flocculation judgement signals, as will be described later in further detail. A stirrer controller 36 determines the number of revolution of each motor 26A, 26B, 26C on the basis of the judgement signals, and controls the speed of each motor.

Figure 2:
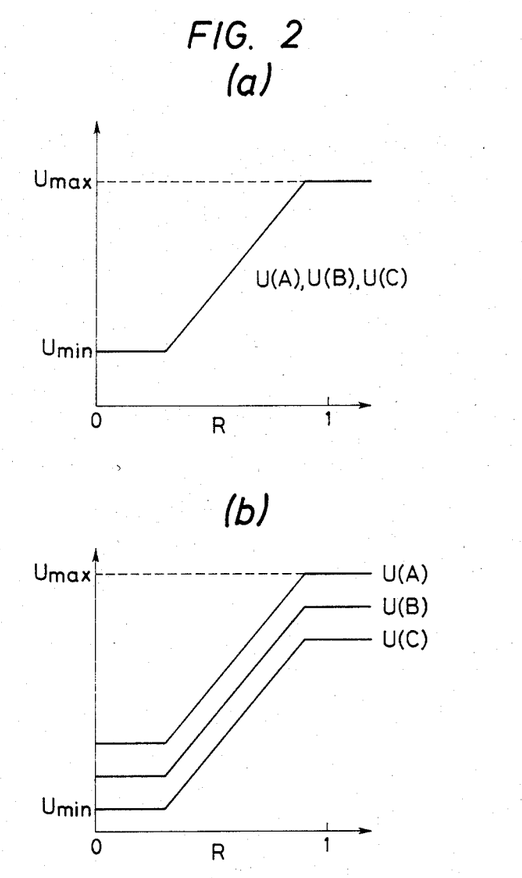
FIG. 2 is an explanatory view for explaining the operation of the control apparatus.

FIG. 2(a) shows the relation between the judgement signal R and the number of revolution of paddle U when the number of revolution of the three motors 26A, 26B, 26C is controlled to the same value with respect to the characteristic value of the particle diameter distribution. In this case, a floc volume distribution ratio (the percentage of the volume of flocs having particle diameters above a certain predetermined diameter to the volume of the whole flocs; the detail will be given elsewhere) is employed as the characteristic value of the particle diameter distribution. As can be seen from the diagram, the ratio of the greater flocs is small when the floc judgement signal is small, so that the number of revolution U(A), U(B), U(C) of each paddle 24A, 24B, 24C is reduced. When the floc judgement signal R is great, on the contrary, it means that the ratio of the greater flocs is great, so that the number of revolution U(A), U(B), U(C) of each paddle 24A, 24B, 24C is increased. Upper and lower limits $U_{max}$, $U_{min}$ are provided for the number of revolution of the paddle 24.

Incidentally, these limits $U_{max}$, $U_{min}$ can not be determined primarily, but are determined empirically and experimentally depending upon a water treatment setup or upon a season, because the water temperature changes with a water source or with a season, and the water viscosity changes with the water temperature. If the water viscosity changes, the fluidizing speed of water changes even if the number of revolution of the paddle is kept constant. In practice, the number of revolution is set in such a fashion that the upper limit $U_{max}$ is 80 cm/sec and the lower limit $U_{min}$ is 15 cm/sec in terms of the peripheral speed of the blade end of the paddle.

In the case of a tapered system in which the numbers of revolution of the stirring paddles 24A, 24B, 24C are mutually different, the numbers of revolution U(A), U(B), U(C) are regulated in accordance with the floc judgement signal R as shown in FIG. 2(b). In other words, the paddles are operated in such a fashion that the number of revolution U becomes smaller on the downstream side of the flocculation basins 20. The operation pattern of the number of revolution for the floc judgement signal R is the same as in FIG. 2a.

Figure 3A:
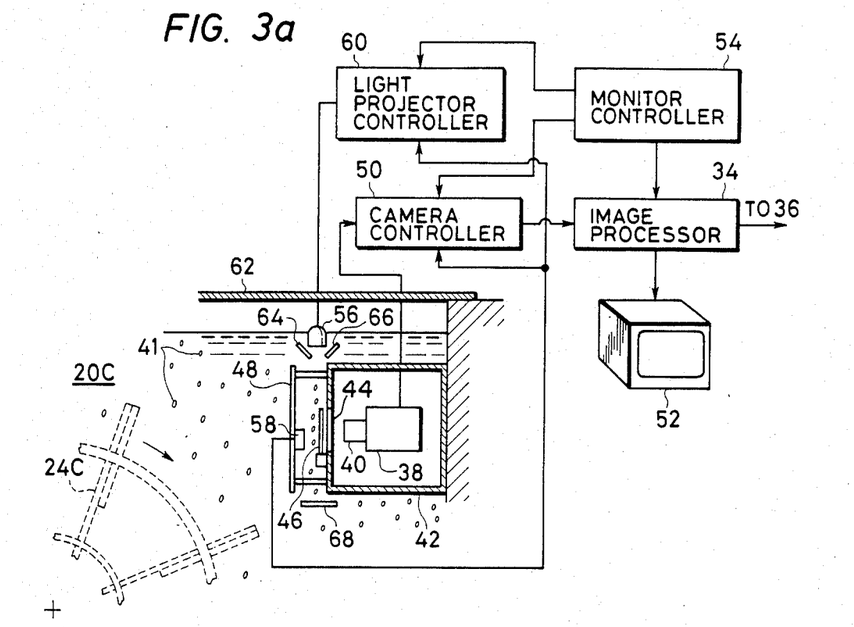
FIG. 3 is a schematic view of a floc monitor used for the embodiment shown in FIG. 1.
Figure 3B:
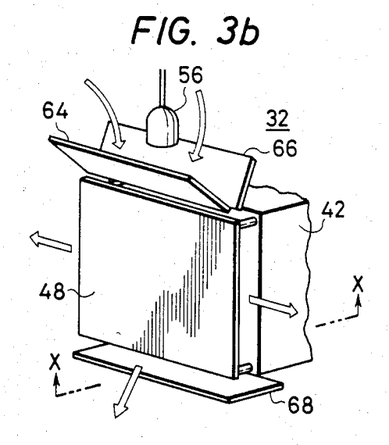
Figure 3C:
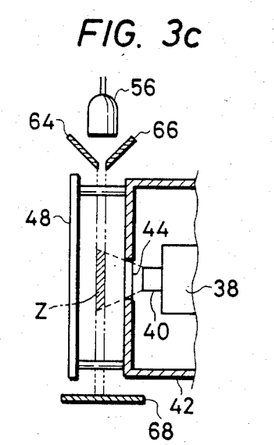

FIGS. 3a–3c show the construction of the floc monitor used in the embodiment described above. In the drawing, like reference numeral is used to identify a like constituent as in FIG. 1.

In FIG. 3a, an ITV camera 38 is used as the imaging device 32. The camera 38 has a close-up lens 40 and takes the image of flocs 41 in magnification. The camera 38 is placed in a water-tight container 42 and is disposed at a suitable underwater position inside the flocculation basin 20C. The water-tight container 42 has a window 44 of a transparent sheet in order to take the image of the state of flocs 41 therethrough. A wiper 46 is adapted to the window 44 to clean any contamination attaching thereto, and is operated with a predetermined interval. The window 44 and a back screen 48 together define the imaging area by the camera 38. The surface of the back screen 48 opposing the window 44 is colored dark by considering the white type flocs in order to take the images having high contrast.

The image information signal from the camera 38 is sent to the image processor 34 through a camera controller 50. After processed by the image processor 34, the signal is sent to the stirrer controller 36 to control the paddles 24A, 24B, 24C, and is also applied to a display 52 to display the result of processing. Reference numeral 54 represents a monitor controller which controls the floc monitor as a whole, and which also controls the image processing in addition to the illumination control of the imaging region to be described next. The detail of the monitor controller 54 will be described in conjunction with the description of the operation of this embodiment.

A light projector 56 illuminates the imaging area. An illuminometer 58 is disposed inside the imaging area, and a light projector controller 60 controls the light projector 56 on the basis of the output signal of the illuminometer 58, so as to stably keep the imaging area at a predetermined intensity of illumination. Any change of illumination of the imaging area exerts a significant influences upon the imaging of flocs. To further stabilize the illumination of the imaging area, a shading cover 62 is disposed in order to shade at least the area from external light. Several examples of shading will be given later with reference to FIG. 14.

Baffle plates 64, 66, 68 are disposed close to the imaging area. When the paddle 24C is rotated in a direction represented by arrow in the drawing inside the flocculation basin 20C, the water in the basin flows clockwise as a whole, so that the water flows from above to below in the imaging area, too. The baffle plates resist the inflow of the water and reduce the velocity of the water in the imaging area.

FIG. 3b is a perspective view showing a part of the imaging device 32 shown in FIG. 3a, and FIG. 3c is a sectional view taken along line X—X. The construction of the baffle plates 64, 66, 68 can be understood clearly from these drawings. The baffle plates 64, 66, 68 are disposed fixedly, of course, by suitable support members, which are not shown in the drawings. The water that inflows from the upper part of the imaging device 32 flows out from the side portion and the lower portion, but is subject to the resistance of the baffle plates 64, 66, 68 so that the flow velocity of water in the imaging area is reduced. In this embodiment, the light projector 56 illuminates the imaging area through the gap defined between the baffle plates 64 and 66. As a result, the camera 38 takes the images of the condition of the focusing zone Z as shown in FIG. 3c.

Figure 4A:
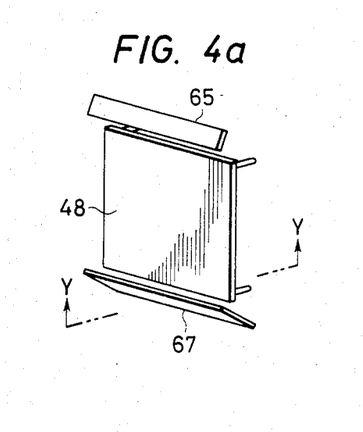
FIGS. 4 through 6 are perspective views showing a partial modified example of the floc monitor.
Figure 4B:
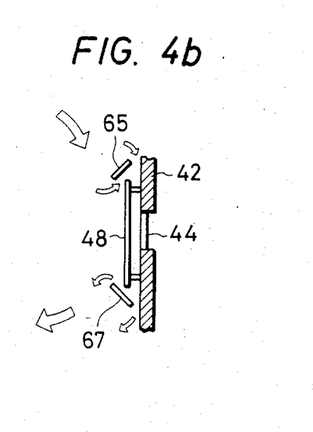
Figure 5:
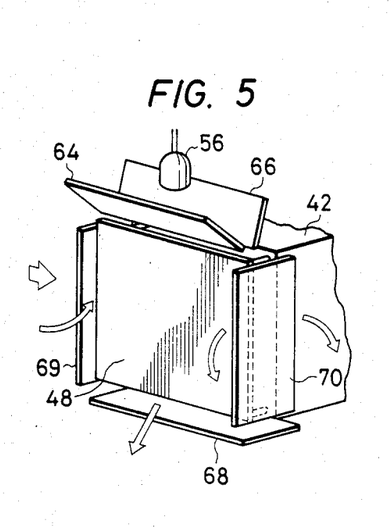
Figure 6:
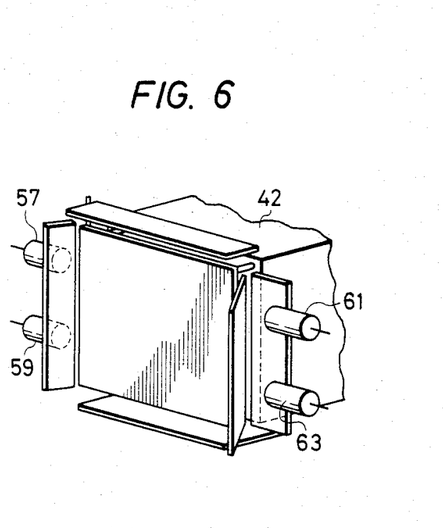

FIGS. 4 through 6 show other constructions of the baffle plates. In FIG. 4a, two baffle plates 65 and 67 are shown employed. FIG. 4b is a sectional view taken along line Y—Y of FIG. 4a and the light from the light projector 56 (not shown) is incident through the gap defined between the baffle plate 65 and the side wall of the container 42. In FIG. 5, five baffle plates 64, 66, 68, 69, 70 are shown employed. In this example, four light projectors 57, 59, 61, 63 are used as the illumination means so as to make uniform the intensity of illumination of the imaging zone.

Since the baffle plates are disposed around the imaging area defined between the back screen 48 and the wall of the container 42 opposing the former, a vortex might be generated particularly at the rear of the baffle plates 64, 66, 65, 69 disposed on the upstream side of the inflowing water. However, any adverse influence of the vortex can be eliminated by securing a sufficiently large imaging area with respect to the focusing zone z, and a stable flow of water can be obtained in the proximity of the focusing zone. The influence of the vortex can be eliminated also by disposing rectification plates in the imaging area in such a manner as not to hinder imaging and light projection.

The operation of the floc monitor having the construction described above will now be explained.

Figure 7:
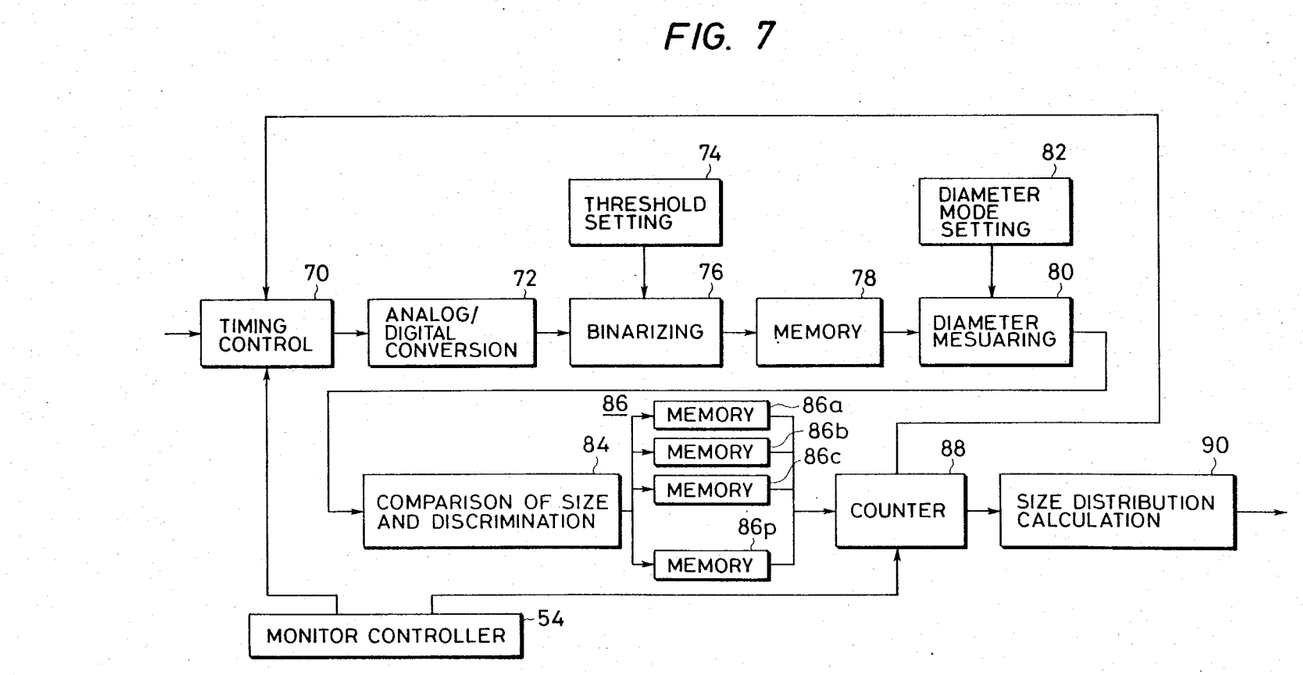
FIGS. 7 and 8 are functional block diagrams of the floc monitor.

FIG. 7 is a functional block diagram of the image processor 34. The image information sent from the camera 38 are generally processed by electronic data processing, but the functional block diagram is used in order to have the present invention more easily understood. In the diagram, reference numeral 70 represents a timing control portion. The image information sent through the camera controller 50 (FIG. 3a) is taken into a next analog/digital conversion portion 72 with such a time interval instructed by the monitor controller 54.

Figure 9A:
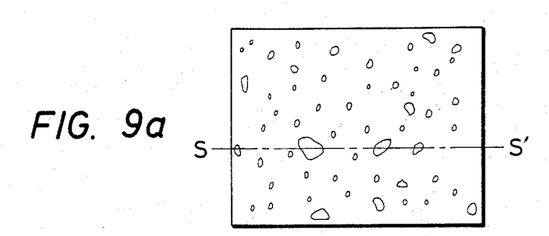
FIG. 9 is an explanatory view useful for explaining the operation of the floc monitor, and particularly for explaining the binarizing processing of floc images.

The A/D conversion portion 72 receives an analog signal obtained as a luminance signal, such as a picture signal shown in FIG. 9a, and coverts it to a digital signal while scanning the picture. The digital signal thus obtained is then binarized by a binarizing portion 76 on the basis of the threshold value designated by a threshold setting portion 74.

Figure 9B:
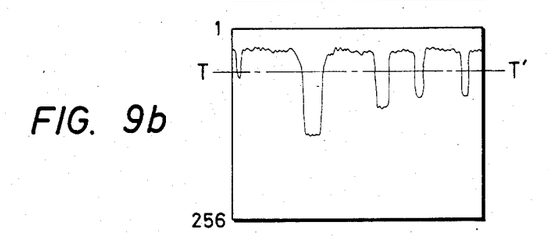

FIG. 9b shows the distribution of the luminance levels when the picture shown in FIG. 9a is scanned along line S—S', for example. Here, the luminance level is represented by 8 bits (256 stages). The luminance is lower at an upper portion of the ordinate and is higher at a lower portion. Since the flocs 41 are rather white, the luminance becomes higher at the portions at which the flocs exist. In other words, valley portions represent the flocs.

In this luminance distribution, each picture element is binarized by a binarizing portion 76 in accordance with the threshold value designated by the threshold setting portion 74 such as the luminance designated by line T—T', for example. The threshold value designated by the threshold setting portion 74 is kept constant under a predetermined intensity of illumination. However, an operator can set the threshold value if an illumination control system including an illuminometer 58 does not exist, or in accordance with other conditions.

Figure 9C:
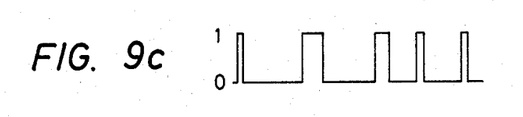

The binarizing portion 76 sets those picture elements which are at higher luminance levels than the threshold value to "1" and those which are lower levels than the threshold value to "0". Then, signals can be obtained representing that the portions corresponding to the flocs are "1" and those corresponding to water, "0", as shown in FIG. 9c. The signals shown in FIG. 9c that are obtained by scanning the entire picture as shown in FIG. 9a are stored in a unit screen of the picture in a memory 78. Since the data is stored in a manner corresponding to each picture element on the scanning screen the shape and area of the flocs can be known from the memory content of the memory 78. When storing the data in the memory 78, labelling is also effected to assign the respective numbers to the individual flocs.

Figure 10:
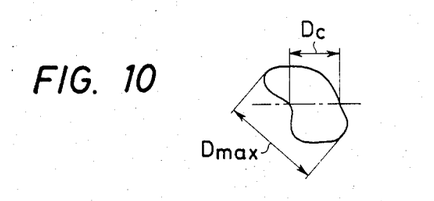
FIG. 10 is an explanatory view useful for explaining the particle diameter of flocs.

A diameter measuring portion 80 calculates the particle diameter d sequentially in the order of the numbers assigned to the individual flocs, on the basis of the memory content of the memory 78. The flocs are generally not complete circle but assume varying shapes. The particle diameter in such a case will be described briefly. In the field of powder engineering, several diameters are assumed for a floc having a shape such as shown in FIG. 10, for example. They are Green size $D_c$ representing a certain diameter in the horizontal direction, a maximum diameter $D_{max}$ representing the greatest particle diameter, a Heywood size $D_{cir}$ represented by $\sqrt{4S/\pi}$ (where S is the area of the floc), and the like. Any of these diameters or sizes may be used in the present invention. In this embodiment, a diameter mode setting portion 82 determines which particle diameter is to be used. The particle diameter d of each floc is calculated in accordance with the standard of the particle diameter thus designated.

Figure 11A:
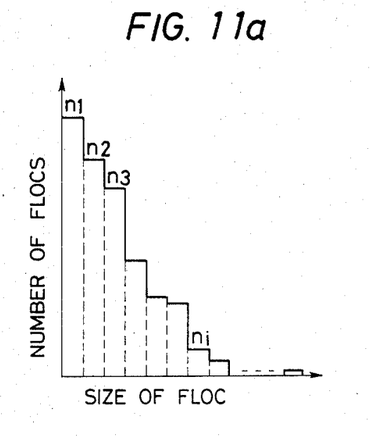
FIG. 11 is an explanatory diagram useful for explaining the particle diameter distribution of the flocs.

A particle diameter comparison and discrimination portion 84 compares the particle diameter d of each floc, and stores the number of flocs having each particle diameter $d_i$ in corresponding positions of memory, that is, number memory portions 86a, 86b, 86c, ..., 86p. Since the image of the floc is binarized, the minimum unit for measuring the particle diameter is one picture element. Therefore, if the number of flocs corresponding to each particle diameter $d_i$ is $n_i$, the number memory portion 86a for example, stores the number $n_1$ of the flocs whose particle diameter corresponds to one picture element, and the number memory portion 86b does the number $n_2$ of the flocs whose particle diameter corresponds to two picture elements. Similarly, the number memory portion 86c stores the number $n_3$ of flocs whose particle diameter corresponds to three picture elements. However, one picture element in the scanning screen corresponds to a predetermined size of the focusing zone$^Z$, it is convenient, when displaying the result of measurement described above by the display 52, to display as the distribution of the number $n_i$ with respect to the practical particle diameters mm or $\mu$m) as shown in FIG. 11a.

The processing described above is one that corresponds to one picture taken at a certain point of time $t_1$. The counter 88 counts the number of times j of this processing. The counter 88 keeps sending signals to the timing control portion 70 whenever one processing is completed, until the counter number j reaches the number of times J which is designated by the monitor controller 54, that is, until the processing of such a number of screens that corresponds to the designated number J is made. Thus, next picture information is taken into, and the processing described above is repeated. The reason why a plurality of image processings are effected within a predetermined period is as follows.

The particle diameters of flocs in the first flocculation basin 20A are from 0.01 to 0.1 mm. On the other hand, the flocs grow to about 1 mm in the third flocculation basin 20C, though they naturally contain a large number of small flocs. Since the particle diameter of flocs is small in the flocculation basin 20A, the number of flocs is sufficiently great. In the flocculation basin 20C, however, the number of flocs is small because their particle diameter is great. To determine accurately the particle diameter distribution of flocs, therefore, the greatest possible number of flocs must be recognized. A preferred number of flocs is at least several hundreds. This can be accomplished by enlarging the picture to be observed, but it becomes difficult, on the contrary, to observe smaller flocs.

Therefore, there is an inherent limit to the size of a picture in which small flocs and great flocs can be recognized with good balance. It can thus be understood that if the floc image information obtained by image processing of only one screen is used, the particle diameter distribution involves large variance and hence is insufficient in order to accurately determine the particle diameter distribution. For these reasons, the information of the floc images obtained by processing of the picture is once stored, and after the processing of the images are repeated several times, the particle diameter distribution is determined on the basis of these memory information.

When the content of the counter 88, that is, the number of times j of the image processing that is effected, reaches the designated number of times J, a size distribution calculator 90 calculates a number density distribution for each particle diameter on the basis of the values of memories 86a, 86b, 86c, ..., 86p. In other words, the number density Ni of the particle diameter $d_i$ is calculated by the following formula:

$$N_i = n_i/w/J \ldots \quad (2)$$

where w is the capacity of the focusing zoneZ by the camera 38.

The particle diameter distribution such as shown in FIG. 11a can be obtained by the processing described above. If the instruction is applied to the stirrer controller 36 on the basis of the value thus obtained, the formation of flocs can be remarkably improved because the instruction is based upon the accurate judgement of the flocculation state.

In the number density distribution, the number of flocs having small particle diameters increases so that it is naturally possible to employ a method which displays the distribution by a volume density distribution by regarding the flocs as balls. This method is conducted in the following manner. The volume of a ball is calculated for each particle diameter by regarding the floc as having such a diameter $d_i$. The volume density $M_i$ of the particle diameter $d_i$ is then calculated on the basis of the volume $m_i$ thus obtained:

$$M_i = m_i \cdot n_i/w/J \ldots \quad (3)$$

Figure 11B:
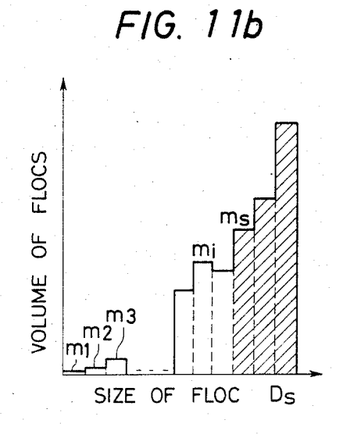

The volume density distribution determined in this manner is shown in FIG. 11b.

An example of the result of experiments carried out for the above-mentioned processing by the inventors of the present invention will be described with reference to FIG. 13. First of all, kaolin was added in a concentration of 5 mg/l as turbid fine particles to water to prepare sample water. The water temperature was 14.9° C. PAC as a coagulant was added in a concentration of 2 ppm to this sample water, and the water was stirred so that the fluidizing speed was 3 to 10 cm/sec. Experiments were started 30 minutes later.

Figure 13A:
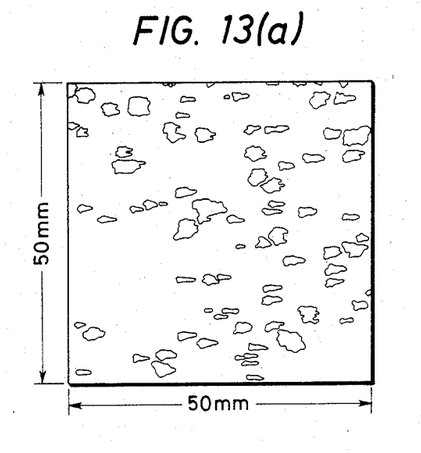
FIG. 13 is an explanatory diagram showing an example of experiments using the floc monitor.

The condition of flocs in the sample water at this point of time was shown in FIG. 13(a). The photo shows the condition of an imaging area of 50 mm by 50 mm. This figure was obtained by binarizing the signals of the images taken by the camera and displaying the result on the display.

Such a condition was photographed with 2 minutes interval, and the processing described already was conducted for each picture with the results being shown in (i) through (vi) of FIG. 11(b). In the diagram, the abscissa represents the particle diameter of the floc, and is plotted in 0.1 mm unit from 0 mm to 5.0 mm. The ordinate represents the volume density expressed by the foregoing formula (3). This is expressed by the ratio of the sum (mm$^3$) of the volumes of flocs having a particle diameter $d_i$(mm) to the volume (cc) of the sample water in the imaging zone.

FIG. 11(b)(i) shows the result when processing was conducted for only one screen that was photographed. The number of flocs recognized in this instance was 105. Thereafter, the screen was increased one by one, and hence (vi) shows the result when the processing was conducted using the six screens. The sum of the number of flocs for the six screens used for the processing was 561. Incidentally, the fluidizing speed of the sample water as maximum 10 cm/sec and one side of the imaging area was 50 mm. Therefore, the time necessary for the floc to pass through the imaging area was 0.5 sec. In contrast, the photographing interval of each screen was two minutes and was sufficiently greater than the time 0.5 sec that was necessary for the floc to pass through the imaging area. This means that each picture always showed a new condition, and that the condition of flocculation was observed over a wide range inside the flocculation basin.

Figure 13B:
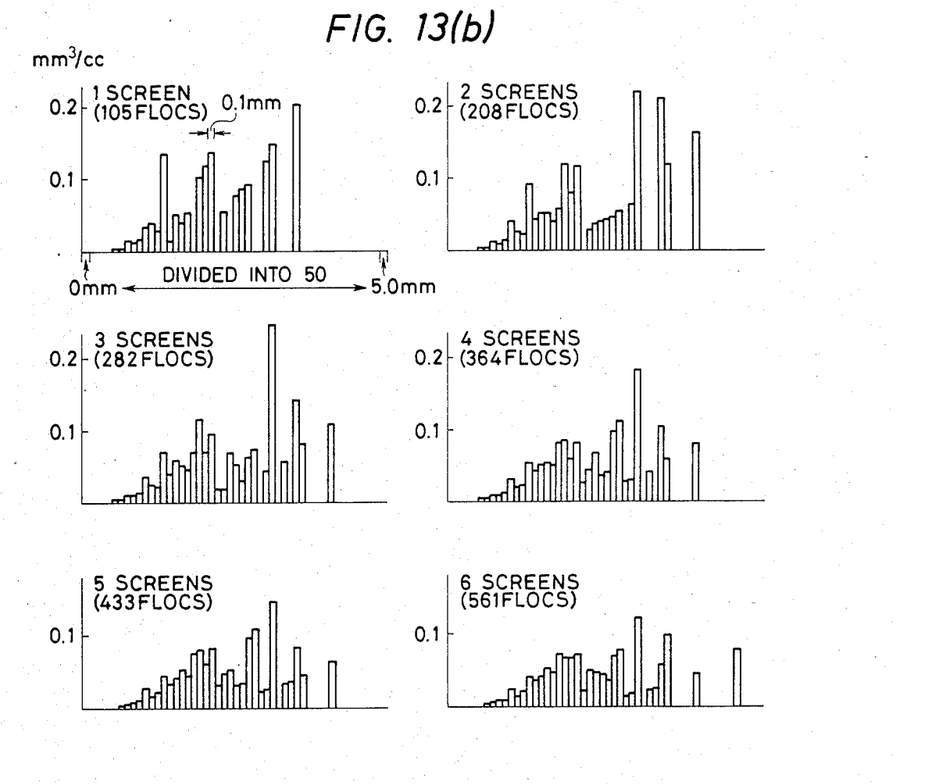

As can be seen from FIG. 13(b), the characteristics of the particle diameter distribution are well shown in (iv) and (vi) when compared, for example, with (i). Though FIG. 13(b) shows the result for the six screens, a greater number of pictures may of course be employed.

Figure 8:
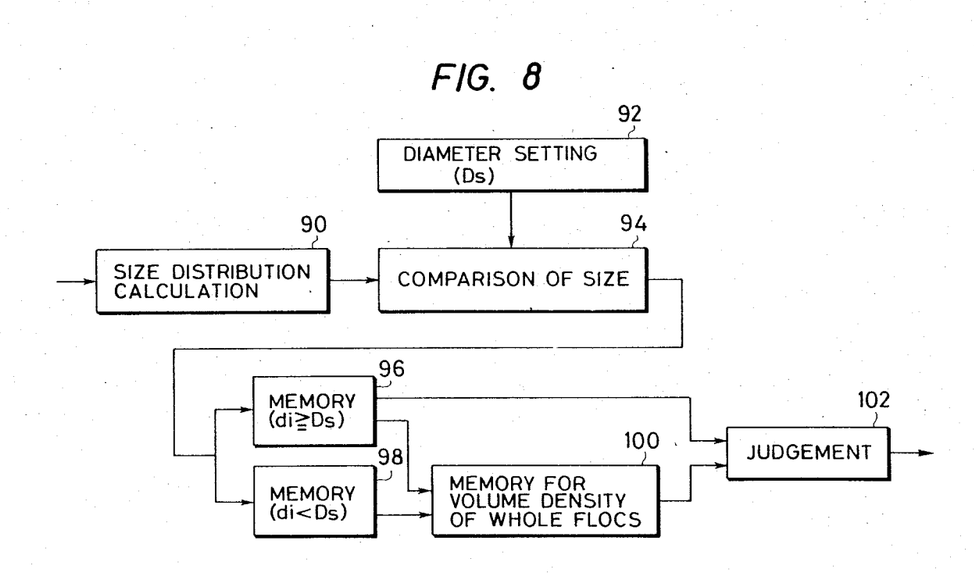

In the embodiment described above, stirring control is directly made on the basis of the particle diameter distribution. However, it is also possible to determine the characteristics values of the particle diameter distribution and to make stirring control on the basis of the characteristics values. This method will now be explained about the case of the volume density distribution with reference to FIG. 8.

In the case of the volume density distribution, the output signal from the size distribution calculator 90 contains the portion corresponding to the particle diameter information and the portion corresponding to the volume density information. Among them, the signal portion corresponding to the particle diameter $d_i$ is compared by a size comparator 94 with a reference particle diameter $D_s$ set by a diameter setting portion 92. The volume density $M_i$ of the flocs having a greater particle diameter $d_i$ than the reference particle diameter $D_s$ is comulatively stored in a memory for volume density of grown-up flocs 98. This is called $M_g$ and corresponds to the area of the hatched portion in FIG. 11b. On the other hand, the volume density $M_i$ of flocs having a smaller particle diameter $d_i$ than the reference particle diameter $D_s$ is cumulatively stored in a memory for volume density of small flocs 98. This is called $M_m$ and corresponds to the area of the portions which are not hatched in FIG. 11b.

Next, the sum $M_t$ of $M_g$ and $M_m$ is calculated, and the result is stored in a memory for volume density of whole flocs 100.

A judgement portion 102 determines the ratio of the grown-up floc density $M_g$ to the total floc density $M_t$, and judges whether or not the ratio is greater than a predetermined value r:

$$M_g/M_t \geq r \ldots \quad (4)$$

When the ratio $M_g/M_t$ is greater than the predetermined value r, it represents that many grown-up flocs exist. Therefore, the flocculation state is regarded as being satisfactory. On the other hand, when the ratio $M_g/M_t$ is smaller than the predetermined value r, it represents that many small flocs exist, on the contrary. Therefore, the flocculation state is regarded as being unsatisfactory. Incidentally, though the judgement whether or not the ratio $(M_g/M_t)$ is greater than the predetermined value may be made in the manner described above, it is also possible to use the ratio itself as the output R of the judgement portion 102 and to use it as the signal for the stirring control. FIG. 2 shows such an example.

Figure 12A:
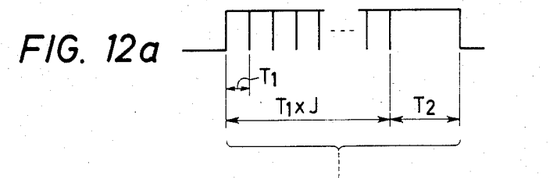
FIG. 12 is a time chart useful for explaining the operation of the floc monitor.
Figure 12B:
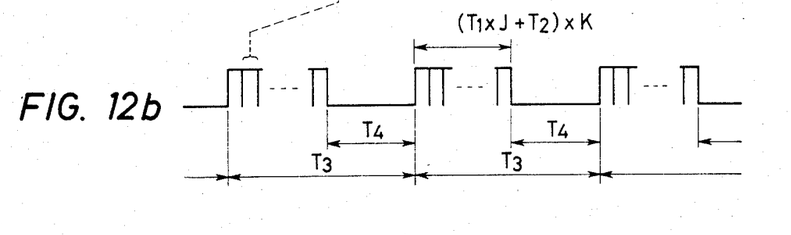

Next, the image taken-in time interval will be described with reference to the time charts of FIGS. 12a and 12b. Let it be assumed that the moving speed of flocs 41 flowing on the front surface of the window 44 (FIG. 3a) is $v_1$ cm/sec and the area of the focusing zone$^Z$ recognizing the images of flocs is $l_1$ cm $\times l_1$ cm. The time $T_1$ required for a given floc to pass from one end of the focusing zone to the other end is given by:

$$T_1 = l_1/v_1 \ldots \quad (5)$$

In other word, if the floc image take-in time interval is set to be greater than $T_1$ in the timing control portion 70 shown in FIG. 7, it is possible to always take in new floc information.

In the embodiment described above, the image processing is effected the J times that are set to the counter 88. Therefore, if the image take-in time interval is set to $T_1$, a time $T_1 \times J$ is necessary for the image processing for recognizing the flocs. Furthermore, processings such as the calculation of the particle diameter distribution, the judgement of the growth of flocs, and the like, are effected on the basis of these recognition data. If a time $T_2$ is assumed necessary for these processings, a series of processings such as the floc recognition and judgement requires a time $(T_1 \times J + T_2)$. However, ordinary processors for effecting the image processing need only several seconds as the time $(T_1 \times J + T_2)$ for the series of these processings.

It is therefore possible to execute sequentially, continuously and repeatedly the subsequent processings after the floc recognition and judgement processing is completed at a certain point of time. Generally, however, the water treatment process control is characterized in that response (such as a time passed before the reaction of chemicals extends to the water treatment process as a whole immediately after the chemical doses) is as long as from several dozens of minutes to several hours. For this reason, it is not much necessary to always repeat the floc recognition and judgement processing, but such a processing may be effected K times with an arbitrary time interval $T_3$. The time necessary therefor is $(T_1.J+T_2)\times K$.

The processor for the image recognition can be utilized highly efficiently and for multiple purposes if the processor is assigned to do other processings (such as tracing of fish to supervise the inflow of poison) by utilizing its idle time.

Figures 14A, 14B:
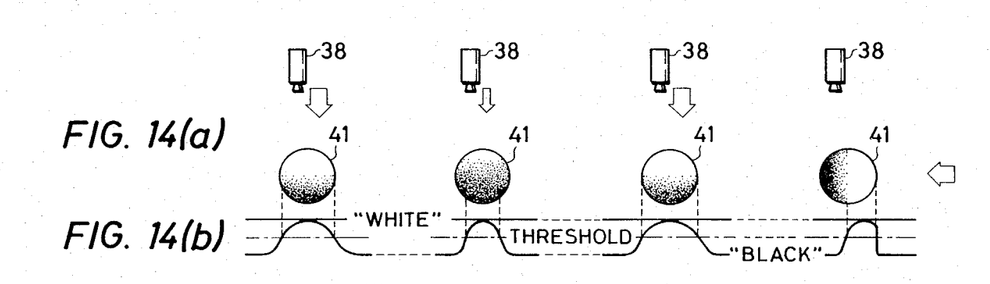
FIG. 14 is an explanatory view useful for explaining the problem due to the intensity and direction of light when photographing the flocs.
Figure 14C:
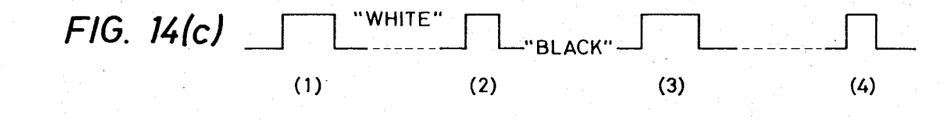

Next, the relation between the detection of flocs 41 by the camera 38 and the light for photographing will be described. As can be understood from FIG. 14, the recognition of flocs 41 is greatly affected by the intensity of light or its direction. In FIG. 14, (a) represents the state when the light is incident to the floc 41 which is assumed spherical. The intensity of light is represented by the thickness of arrow, and its projecting direction, by the direction of the arrow. (b) represents a luminance signal obtained from the image information obtained by photographing the floc 41 by the camera 38. (c) represents a binarized signal obtained by binarizing the luminance signal of (b) at a predetermined threshold level. If the intensity of light is great (FIG. 14 (1)), the floc 41 is likely to be recognized greater than as it actually is, and if the intensity is small (FIG. 14 (2)), the floc is likely to be recognized smaller. Therefore, the intensity of light must be kept uniform and constant in the imaging zone. The disposition of a plurality of illumination means and the illumination control by feeding back the intensity of illumination of the imaging zone by the illuminometer, that are described earlier, are effective for this purpose.

The projecting direction of light is to be considered in conjunction with the photographing direction. If the projecting direction is parallel to the photographing direction (FIG. 14(3)), it is likely that the floc 41 is recognized to be greater than as it actually is, and if the former is perpendicular to the latter, it is likely that the floc 41 is recognized to be smaller (FIG. 14(4)). Therefore, the incident to the flocculation basin 20C (more accurately, the basin in which the imaging device 32 (FIG. 1) is disposed) must be taken into consideration. However, since the direction of the sunbeams changes all the day, the accuracy of floc recognition can be improved by disposing shading means which shades at least the imaging zone Z from the sunbeams.

Figure 15A:
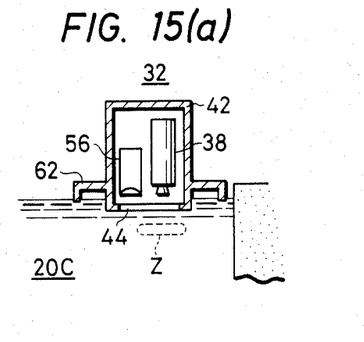
FIG. 15 is a schematic view showing several examples of a shading cover for solving the problem described above.

FIGS. 15(a) through 15(e) show several examples of shading means. In FIG. 15(a), the camera 38 and the projector 68 are shown incorporated integrally in one watertight container 42 and the shading cover 62 is disposed in the flocculation basin 20C in such a manner as to sufficiently shade at least the imaging zone Z. Though the integral container 42 is supported by suitable support members, such members are omitted in the drawing. They are not shown, either, in the following examples.

Figure 15B:
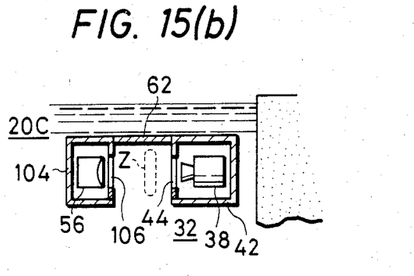

In FIG. 15(b), the projector 56 is shown incorporated in a water-tight container 104 which is separate from that of the camera. The container 104 has a window 106 for projecting light. The window 44 of the water-tight container 42 storing therein the camera 38 and the window 106 of the container 104 storing therein the projector 56 face each other, and the imaging zone Z is defined between them. These two containers 42 and 104 are connected by a suitable connecting member, which plays the role of the shading cover 62. Unlike the example described above, this example the shade portion of the floc but does not catch the reflected light from the floc. In this case, too, the afore-mentioned problem arising from the relation between the projecting direction and the photographing direction also exists, as can be understood easily from FIG. 14.

Figure 15C:
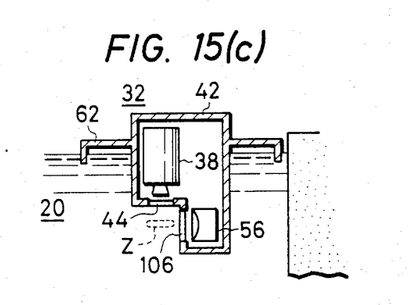

FIG. 15(c) shows another example in which the camera 38 and the projector 56 are stored in the integral water-tight container 42 in the same way as in the example shown in FIG. 15(a). However, the projecting direction is prependicular to the photographing direction.

Figure 15D:
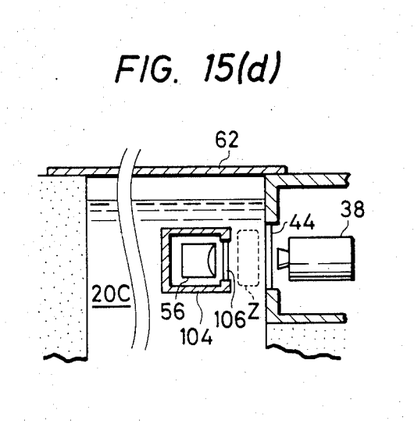
Figure 15E:
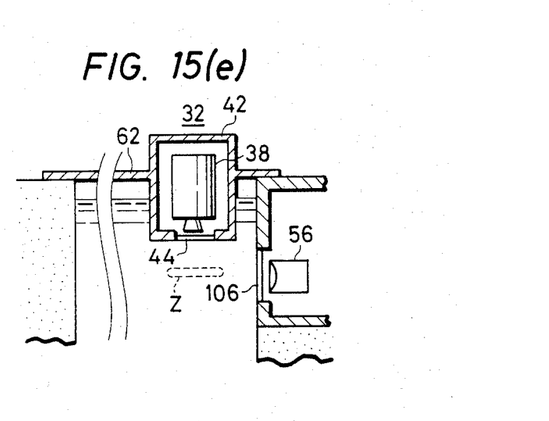

Unlike the examples described above, the shading cover 62 that fully covers the flocculation basin 20C as a whole, in which the imaging device 32 is disposed, is shown disposed in FIGS. 15(d) and 15(e). In FIG. 15(d), the camera 38 is disposed inside the side wall of the flocculation basin 20C, and photographing is effected through the window 44 which is formed at a part of the side wall. In FIG. 15(e), the projector 56 is shown disposed inside the side wall of the flocculation basin 20C, contrary to FIG. 15(d).

The relation of positions of the camera 38, the projector 56 and the shading cover 62 is not particularly limited to that in the above-mentioned examples, but suitable combinations or other examples which eliminate the adverse influences of the sunbeams can of course be employed in the light of the gist of the present invention.

As described above, the present invention can drastically improve the formation of flocs because the stirrer is controlled in accordance with the state of formation of flocs in such a manner as to change the fluidizing speed of water in the flocculation basin.

The state of the formation of flocs can be made more accurate and the flocculation can be further improved because the particle diameter distribution of flocs is detected from a sufficiently large number of flocs.

What is claimed is:

1. A flocculating system in a water treatment process comprising:
    a flocculation basin into which water containing coagulants and suspended particles is introduced;
    means for taking a plurality of pictures of a predetermined zone inside said flocculation basin within a predetermined interval of time;
    means for obtaining and storing a particle diameter distribution of flocs shown in each of the pictures;
    means for producing an output signal based on the particle diameter distribution of the flocs;
    flocculater means for mixing the water inside said flocculation basin in such a manner that the flocs impinge against one another and grow to greater flocs; and
    flocculater control means for controlling said flocculater means on the basis of the output of said signal producing means and changing the mixing speed of the water inside said flocculation basin.

2. The flocculating system in a water treatment process as defined in claim 1 further comprising baffle plates exhibiting resistance to the water flowing into said predetermined zone and reducing the mixing speed of the water inside said predetermined zone.

3. The flocculating system in a water treatment process as defined in claim 1 wherein said flocculater means includes a plurality of flocculaters, said flocculation basin consists of a plurality of unit basins that are cascaded by a flow passage, each of said unit basins is equipped with a flocculater, and said flocculater of each of said unit basins is controlled in such a manner that the mixing speed of the water inside each of said unit basins decreases progressively from said unit basin on the uppermost stream side to said unit basin on the downmost stream side.

4. The flocculating system in a water treatment process as defined in claim 1, further comprising means for introducing water containing coagulents and fine particles into the flocculation basin and means for removing water containing flocs from the flocculation basin.

5. A floc monitor for use in a water treatment process comprising:
- area defining means for defining a predetermined area within a flocculation basin in a water treatment process to cause water to flow in a substantially predetermined direction inside the predetermined area;
- means for taking a plurality of pictures of the predetermined area within a predetermined interval of time;
- means for obtaining and storing a particle diameter distribution of flocs shown in each of the pictures; and
- means for producing an output signal based on the particle diameter distribution of said flocs; said signal being representative of the growth state of the flocs, and enabling monitoring of the growth state of the flocs in said flocculation basin.

6. The floc monitor for use in a water treatment process as defined in claim 5 which further includes illumination means for illuminating said predetermined area.

7. The floc monitor for use in a water treatment process as defined in claim 6 which further includes:
- an illuminometer detecting the intensity of illumination of said predetermined area; and
- illumination control means for controlling said illumination means on the basis of the output of said illuminometer in such a manner as to keep the intensity of illumination of said predetermined area substantially constant.

8. The floc monitor for use in a water treatment process as defined in claim 5 which further includes a shading cover shading at least the portions which are in the proximity of said predetermined area from external light.

9. The floc monitor for use in a water treatment process as defined in claim 5 which further includes means for setting said predetermined interval of time to be greater than the time required for flocs to pass through said predetermined area.

10. The floc monitor for use in water treatment process as defined in claim 5 wherein said means for producing an output signal determines a reference particle diameter, calculates the proportion of flocs having particle diameters greater than said reference particle diameter to all those flocs which are observed, and produces a signal of this proportion representing the growth state of flocs.

11. A floc monitor for use in a water treatment process comprising:
- area defining means for defining a predetermined area inside a flocculation basin in a water treatment process to cause water to flow in a substantially predetermined direction inside the predetermined area;
- baffling means for exhibiting predetermined resistance against at least the flow of water and reducing the flow velocity of the water flowing through the predetermined area;
- imaging means for taking pictures of the predetermined area and producing image information signals thereof; and
- signal processing means for producing signals representing the growth state of flocs inside the flocculation basin on the basis of the image information signals, and enabling monitoring the growth state of said flocs.

12. The floc monitor for use in a water treatment as defined in claim 11 which further includes illumination means for illuminating said predetermined area.

13. The floc monitor for use in a water treatment process as defined in claim 12 which further includes:
- an illuminometer for detecting the intensity of illumination of said predetermined area; and
- illumination control means for controlling said illumination means on the basis of the output of said illuminometer in such a manner as to keep of the intensity of illumination of said predetermined area substantially constant.

14. The floc monitor for use in a water treatment process as defined in claim 11 which further includes a shading cover shading at least those portions which are in the proximity of said predetermined area from external light.

* * * * *